United States Patent [19]

Brennen et al.

[11] Patent Number: 5,396,902
[45] Date of Patent: Mar. 14, 1995

[54] STEERABLE STYLET AND MANIPULATIVE HANDLE ASSEMBLY

[75] Inventors: Kenneth R. Brennen, Fridley; Peter J. Pohndorf, Stillwater; Kenneth B. Stokes, Brooklyn Park, all of Minn.

[73] Assignee: Medtronic, Inc., Minneapolis, Minn.

[21] Appl. No.: 69,310

[22] Filed: May 28, 1993

Related U.S. Application Data

[63] Continuation-in-part of Ser. No. 13,126, Feb. 3, 1993.

[51] Int. Cl.⁶ .............................................. A61B 5/00
[52] U.S. Cl. ........................................................ 128/772
[58] Field of Search ................ 128/657, 772; 604/95, 604/280-283

[56] References Cited

U.S. PATENT DOCUMENTS

| | | | |
|---|---|---|---|
| 1,832,533 | 11/1931 | Creasy . | |
| 2,118,631 | 5/1938 | Wappler | 128/349 |
| 2,498,692 | 2/1950 | Mains | 128/348 |
| 2,847,990 | 8/1958 | Ayre | 128/2 |
| 3,416,531 | 12/1968 | Edwards | 128/348 |
| 3,452,740 | 7/1969 | Muller | 128/2 |
| 3,503,385 | 3/1970 | Stevens | 128/2 |
| 3,521,620 | 7/1970 | Cook | 128/2.05 |
| 3,528,406 | 9/1970 | Jeckel et al. | 128/341 |
| 3,547,103 | 12/1970 | Cook | 128/2.05 |
| 3,552,384 | 1/1971 | Pierie et al. | 128/2.05 |
| 3,605,725 | 9/1971 | Bentov | 128/657 |
| 3,749,086 | 7/1973 | Kline et al. | 128/2 |
| 3,789,841 | 2/1974 | Antoshkiw | 128/2.05 |
| 3,841,308 | 10/1974 | Tate | 128/2 |
| 4,136,703 | 1/1979 | Wittkampf | 128/419 |
| 4,215,703 | 8/1980 | Willson | 128/772 |
| 4,245,624 | 1/1981 | Komiya | 128/4 |
| 4,350,169 | 9/1982 | Dutcher et al. | 128/783 |
| 4,357,947 | 11/1982 | Littleford | 128/786 |
| 4,381,013 | 4/1983 | Dutcher | 128/785 |
| 4,422,460 | 12/1983 | Pohndorf | 128/786 |
| 4,506,680 | 3/1985 | Stokes | 128/786 |
| 4,577,642 | 3/1986 | Stokes | 128/784 |
| 4,606,118 | 8/1986 | Cannon et al. | 29/825 |
| 4,624,266 | 11/1986 | Kane | 128/785 |
| 4,677,990 | 7/1987 | Neubauer | 128/786 |
| 4,733,669 | 3/1988 | Segal | 128/663 |
| 4,799,496 | 1/1989 | Hargreaves et al. | 128/772 |
| 4,807,626 | 2/1989 | McGirr | 128/328 |
| 4,813,434 | 3/1989 | Buchbinder et al. | 128/772 |
| 4,815,478 | 3/1989 | Buchbinder et al. | 128/772 |
| 4,824,435 | 4/1989 | Giesy et al. | 604/49 |
| 4,846,175 | 7/1989 | Frimberger | 128/303.15 |
| 4,886,067 | 12/1989 | Palermo | 128/657 |
| 4,921,482 | 5/1990 | Hammerslag et al. | 604/95 |
| 4,976,691 | 12/1990 | Sahota | 604/96 |
| 5,195,968 | 3/1993 | Lundquist et al. | 128/772 |
| 5,277,199 | 1/1994 | DuBois et al. | 128/657 |

FOREIGN PATENT DOCUMENTS 0274705 12/1987 European Pat. Off. .
2647005  5/1989 France .
3920707 10/1991 Germany .

*Primary Examiner*—Max Hindenburg
*Attorney, Agent, or Firm*—Michael J. Jaro; Harold R. Patton

[57] ABSTRACT

A steerable stylet and manipulative handle assembly for guiding a lead or a catheter to a desired location in a patient. The steerable stylet comprises an outer, elongated tubular member of a length sufficient to extend through the length of the lead or catheter from its proximal opening to the distal end thereof, a traction element or pull wire extending generally through the length of the tubular member and within its lumen except for a span in the distal portion thereof, and a manipulative handle coupled to the proximal ends of the tubular member and wire. Traction applied with one hand to the pull wire via the handle causes the distal portion of the tubular member to bend. Distal portion of the tubular member is provided with openings to allow the wire to exit and re-enter the lumen and facilitate bending of the tubular member. Distal portion of the tubular member which bends is preferably deformed, such as cut out or flattened or indented, to avoid kinking. A retainer surrounds the area proximate the openings and protects the exposed pull wire.

22 Claims, 13 Drawing Sheets

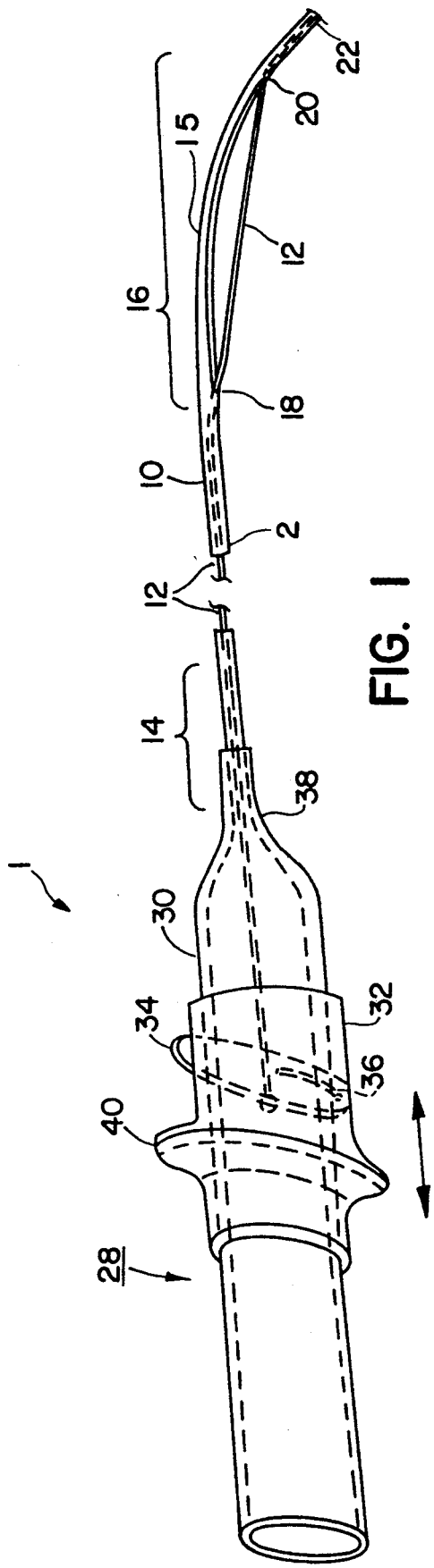

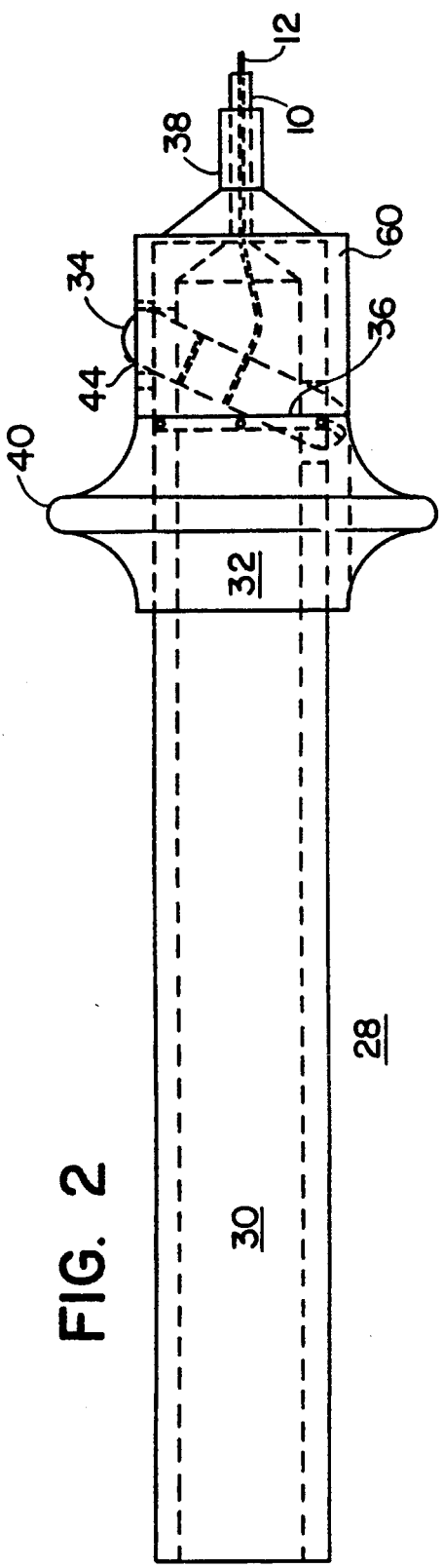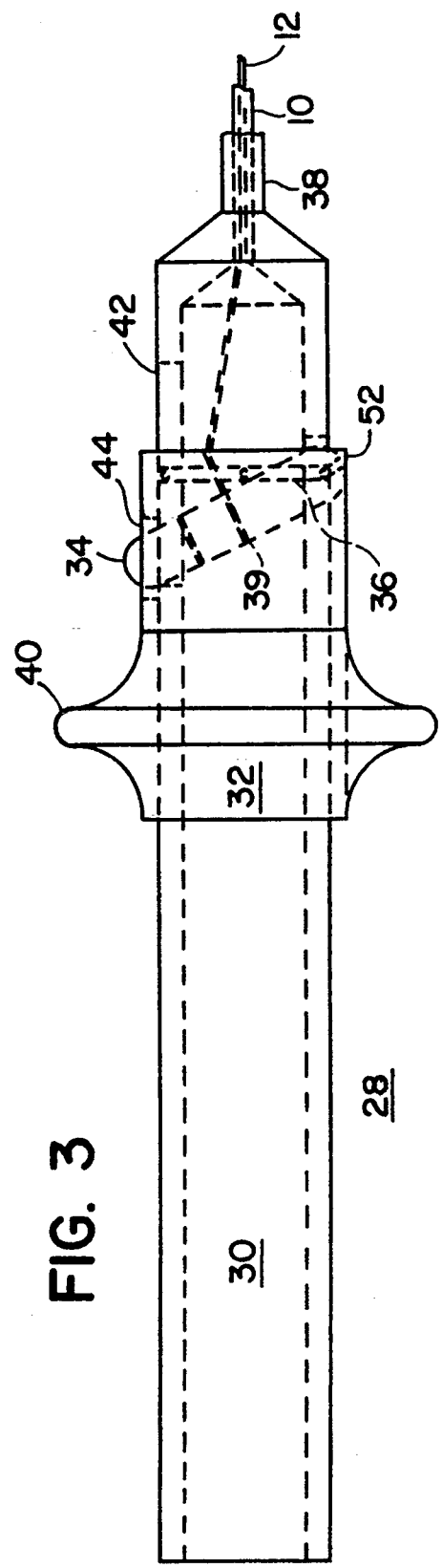

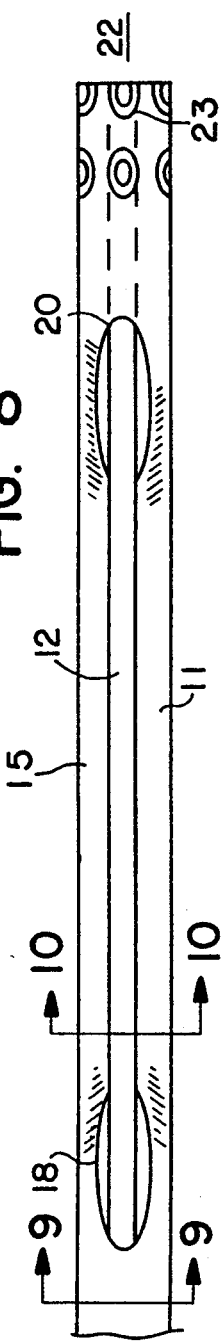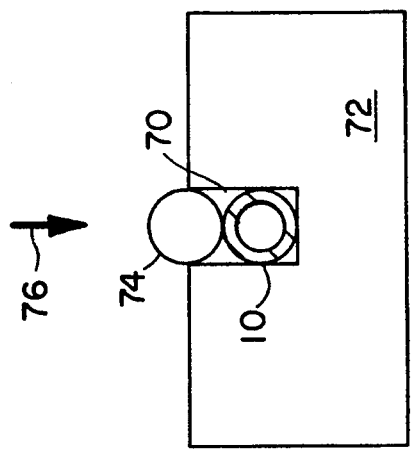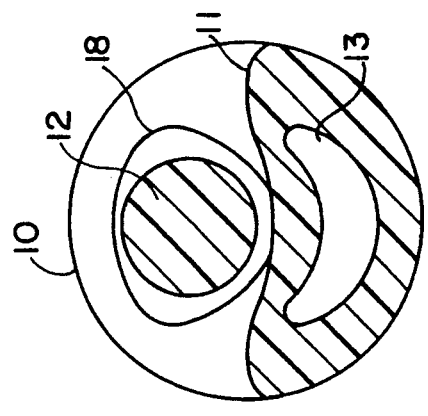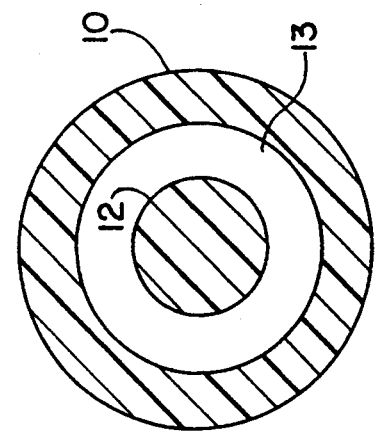

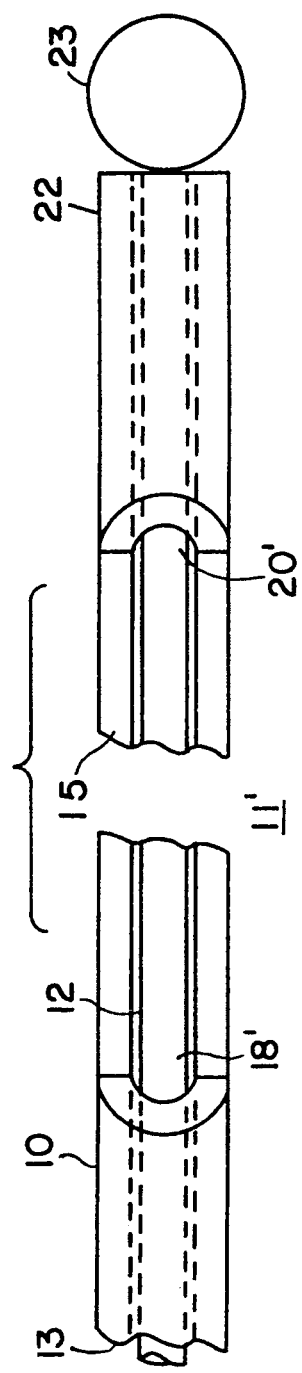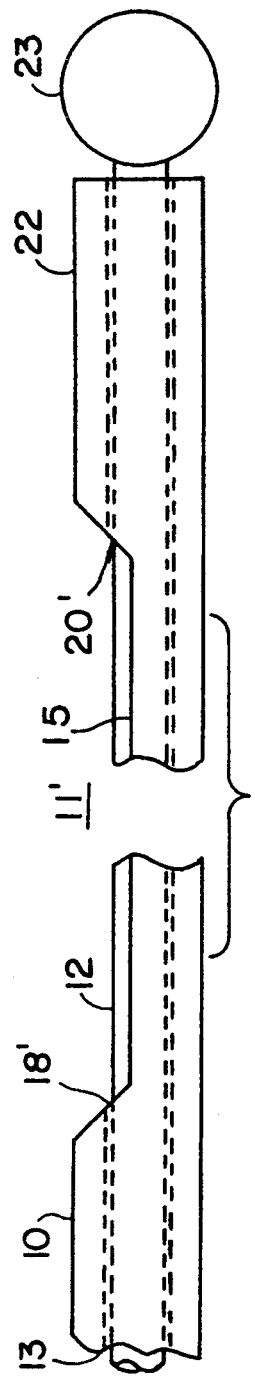

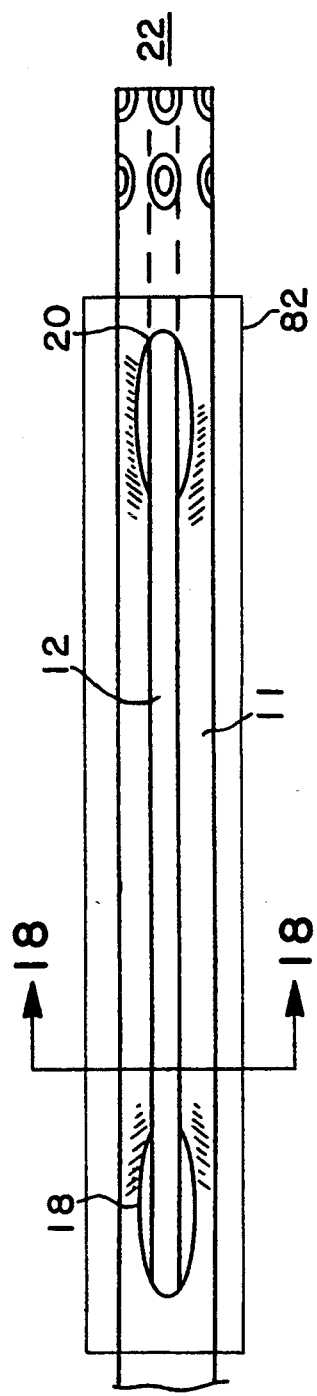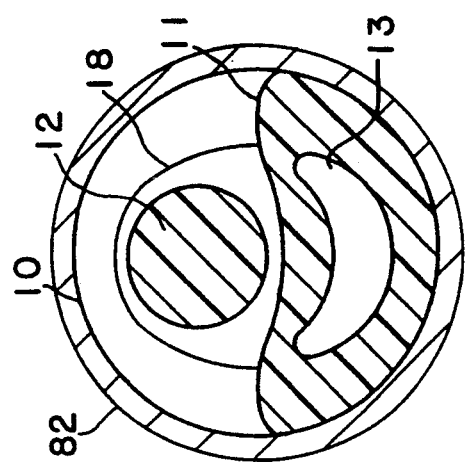

STEERABLE STYLET AND MANIPULATIVE HANDLE ASSEMBLY

REFERENCE TO RELATED APPLICATIONS

This is a continuation-in-part of copending application Ser. No. 08/013,126, filed Feb. 3, 1993.

BACKGROUND OF THE INVENTION

1. Field of the Invention

The present invention relates to a wire guide or stylet assembly for the introduction of medical catheters or electrical leads to a desired site within a patient's body, and specifically to a steerable stylet assembly for imparting a desired dynamic curvature in the distal portion of a catheter or lead during its introduction in order to guide it through curvature in the patient's vascular system and to a desired site in the patient's cardiovascular system.

2. Description of the Prior Art

The marked advances in cardiac and vascular surgery in the past few years and other medical problems that require diagnostic study of the vascular beds and systems as well as the advances in pacing and cardioversion, has led to the extensive use of cardiac or vascular catheters, such as percutaneous transluminal coronary angioplasty (PTCA) catheters and transvenous or endocardial pacing and cardioversion leads. The insertion of a relatively long catheter or lead body to an internal site requires advancement of the catheter or lead into branch vessels at varying angles relative to the feeding direction of the catheter or a lead.

In respect to the introduction of PTCA catheters, for example, several techniques for introducing such catheters are available, including the cut-down method and the Seldinger techniques. The Seldinger technique involves puncturing a vein or artery with a needle, inserting a guide wire into the vein or artery through the lumen of the needle, withdrawing the needle, inserting over the guide wire a dilator located inside a sheath, removing the dilator and inserting a catheter or lead through the sheath into the blood vessel. In this procedure, flexible spring guide wires, of the type disclosed in commonly assigned U.S. Pat. No. 4,815,478 to Buchbinder, et al, and the numerous patents referenced therein, are steered to the desired internal site by remotely deflecting the tip of the guide wire to facilitate movement of the guide wire around or through a curved path in the blood vessel. The steerable spring guide wire of the '478 patent possesses a flexible tip constructed with flexible spring coil wire extending from a flexible elongated tubular body and coupled to a long tip which is additionally coupled to a deflection wire extending through the flexible tubular body and the spring coil as well as a control wire extending through the lumen to provide for the deflection of the distal tip portion by the application of traction to the proximal end of the control wire. The control wire remains within the confines of the tubular body as well as the loosely-wound flexible spring coil distal portion thereof. As stated above, once the distal portion of the guide wire is advanced to the desired internal site, then the lumen of the tubular catheter is advanced over the guide wire until its distal tip is advanced to the desired internal site, whereupon the guide wire is withdrawn.

In the pacing and cardioversion context, it is well known to guide the insertion and proper placement of an endocardial lead to a desired internal site in a chamber of the patient's heart or in a vessel, such as the coronary sinus, through the use of a stiffening stylet inserted into the lumen of the pacing or cardioversion lead. Generally speaking, it is highly desirable that pacing and cardioversion leads be so flexible through their length that they are capable of flexing with the movement of the heart and other muscular movement so as to avoid the fracture of the lead body due to its cumulative stressing. Thus, implantable pacing and cardioversion leads are often too limp to be advanced on their own through the venus system to the desired internal site and it has been commonplace for many years to employ thin wire stylets extended down the lumen of the lead to stiffen the entire assembly and to impart a desired degree of curvature of the tip of the lead body during insertion. To accomplish this desirable result, the solid inner stylet wire is given a bend or curvature near its distal end by the physician when it is outside the lumen. After insertion through the lumen, the curved distal portion facilitates movement of the distal tip of the lead through blood vessels into chambers as the lead is advanced and thereafter assists in directing the lead tip to the desired internal site within the patient's heart or cardiovascular system.

It is also commonly known to employ a stylet to straighten an atrial pacing lead, which is provided with a permanent "J"-shaped bend to facilitate both the positioning and the retention of the atrial electrode in the patient's atrial appendage as taught, for example, in U.S. Pat. No. 4,136,703, to Wittkampf. Insertion of these "J"-shaped leads is greatly facilitated through the use of a straight solid inner stylet which, in this case, straightens the bend normally fixed within the distal end of the lead itself.

Such transvenous pacing and cardioversion leads typically comprise a length of coiled wire conductor formed around an axial lumen and encased within a suitable insulating material, such as silicone rubber or polyurethane, that is substantially biocompatible and stable to body fluids and tissues. A hollow connector pin is attached coaxially into the lumen and electrically to the proximal end of the conductor. An electrically conductive electrode at the distal end of the conductor is adapted to be placed in contact with the endocardium or within the coronary sinus of the patient. Generally, when more than one length of separately-insulated coiled wire conductors are employed in modern pacing and cardioversion leads, each coiled wire conductor is wound coaxially around the centrally-disposed lumen which extends through the connector pin and the corresponding lengths of coiled wire conductors to the distal end of the lead body. The lumen receives the stiffening stylet, typically a cylindrical wire, for imparting stiffness and curvature to the distal portion of the lead body to facilitate its advancement through the venous system and to the desired internal site. Further details of the construction and utility of such endocardial pacing leads may be obtained by reference to U.S. Pat. Nos. 4,506,680 and 4,577,642 to Stokes; 4,606,118 to Cannon et al; and 4,711,281 to Kessel et al. each incorporated herein by reference.

Insertion of such endocardial pacing and cardioversion leads frequently requires the physician to commence the introduction through a lead introducer inserted into a vein through a skin puncture. At the outset, the stylet may be straight or curved to facilitate the introduction into the vein and through the initial curvature thereof. Thereafter, and from time to time, as the physician directs the distal tip of the lead to the desired location, it may be necessary to withdraw the stylet and substitute a new stylet having a different curvature, reinsert it, and advance the distal portion of the lead a bit further until another obstacle to advancement is encountered.

This technique, however, has several drawbacks. For example, repeated insertion and withdrawal of the stylet may contaminate the lumen with blood. This is undesirable because drying blood can jam the stylet within the pacing lead, making stylet removal difficult and possibly rendering the lead unusable. Moreover, the continual insertion and withdrawal of stylets is time consuming and offers the potential of damaging the lead or blood vessel or both in the process.

In order to avoid repeated withdrawal and reintroduction of stylets, various approaches have been proposed including those disclosed in commonly assigned U.S. Pat. No. 4,381,013 to Dutcher and U.S. Pat. No. 4,677,990 to Neubauer. The '013 patent discloses use of a two-piece stylet having an inner solid portion for enabling a shape to be imparted to the lead to facilitate introduction in the fashion as described above and an outer tubular portion which enables the transmission of torque applied by the physician at the proximal end of the stylet to be transmitted to a helical fixation means located at the distal end of the lead. The transmission of this torque allows the helical fixation means to be screwed into the endocardial tissue. Thus the inner solid wire stylet operates in the same fashion as the conventional solid wire stylets described above.

The '990 patent discloses the combination of a removable stylet stiffening wire and one or more threads having very low elasticity which are coupled near the distal end of the lead or at selective locations along the lead body extending for a portion of the length of the lead within the lead lumen and for a further portion outside the lumen but within the outer insulative sheath. With the stylet inserted, traction applied to the proximal portion of the thread or threads imparts a curvature into the lead body as the thread is pulled taut. The curvature is dictated by the locations at which the thread or threads are directed in the space between the outer insulative sheath and the coiled wire conductor. To achieve easier bending, the stylet is described as having portions of reduced thickness along its length in parallel with the location of the threads passage outside the lumen.

The '990 patent addresses concerns raised by the conventional technique of withdrawing, imparting a new curve, and reinserting the stiffening stylet during the implantation procedure.

The use of the separate thread and stylet in the '990 patent and the two-piece stylet of the '013 patent, as well as the conventional one-piece stylets, usually require the physician to employ both hands in manipulating the lead and stylet to advance and withdraw the stylet and rotate the lead body in manipulating the advancement of the distal portion of the lead through the venus system or into particular desired sites for lodging the electrodes. U.S. Pat. No. 3,452,740 to Mueller discloses a spring guide manipulator for imparting a curvature and rotation in a spring guide by one-handed use of a manipulative handle. The spring guide wire includes the conventional inner straight wire coupled to the distal end of the coiled wire of the distal portion of the spring wire guide. When the handle is attached to a guide wire and a catheter is fitted over the guide wire, it is reported that the handle may be employed to both rotate the guide wire and catheter as well as place a curve in the distal portion of the catheter.

A further example of a steerable device is disclosed in U.S. Pat. No. 4,846,175 to Frimberger. That patent discloses a steerable probe which, in one embodiment, has an elongated, flattened cross-section and a pull wire exposed to the exterior between two openings. The '175 devices further uses the exposed pull wire to electrically cut tissue, such as a gallstone.

Despite these devices, a need remains for a simple and reliable easy-to-use steerable stylet or catheter guide wire assembly which provides a wide degree of dynamic curvature to the lead or catheter being advanced by the physician.

SUMMARY OF THE INVENTION

It is therefore an object of the present invention to provide a simple and easy-to-use steerable stylet and manipulative handle assembly for imparting a dynamic curvature to the distal portion of a lead or catheter during its advancement through a blood vessel.

It is a further object of the present invention to make such stylet and manipulative handle assembly easy-to-use with one hand.

It is a still further object of the present invention to provide such a stylet and manipulative handle assembly of the character stated which is simple in design, reliable, rugged in construction and economical to manufacture.

These and other objects of the present invention are realized in a stylet for the advancement of a catheter or a lead having a lumen extending therein between a proximal and distal end thereof, wherein the stylet comprises an elongated tubular member having a proximal end and a distal end, with at least one aperture or opening located from the distal end of said tubular member, a traction element or pull wire attached at the distal end of said tubular member and extending loosely outside said lumen for a distance and to the proximal end of the tubular member. The stylet further features a manipulative handle assembly coupled to the proximal end of said tubular member, the manipulative handle compromising a body member attached to said proximal end of said tubular member and receiving said proximal end of said wire therewithin, a slide member adapted to slide along said body member through manipulation thereof by the physician and a control lever pivotally attached to said body member, fixedly attached to said pull wire and loosely coupled to said sliding member.

In the preferred embodiments thereof, the tubular member preferably possesses a second aperture more distally located than the first aperture and the pull wire extends from the distal end of the tubular member through the lumen, out the second aperture, alongside the outer surface of the tubular member, through the first aperture and back within the lumen so that when traction is applied to the pull wire, it tends to cause the tubular member along the deformed portion to bow outward and away from the taut pull wire lying outside the lumen. The pull wire may be fixedly attached to the distal tip of the tubular wire or it may be coupled to an enlarged member that is too large to pass through the lumen of the tube and bears against the distal end when traction is applied, but otherwise may allow the advancement of the distal end of the pull wire beyond the distal end of the tubular member.

In further preferred embodiments of the present invention, the tubular member is deformed in cross-section, such as cut-out, flattened or indented section, between the first and second apertures therein.

In an additional preferred embodiment of the present invention the tubular member has a retainer keeping the stylet isodiametric in the region between the apertures or openings. The retainer further functions as a lubricous solid to facilitate rotation of the lead coil around the stylet even when deflected.

In a still further preferred embodiment the manipulative handle assembly couples with a turning knob to fix a Bisping-type or Dutcher-type screw-in lead.

In accordance with the practice of the present invention, the distal portion and length of the tubular member and pull wire stylet may be introduced into the lumen of a lead or catheter and the proximal end thereof may be coupled to the housing of the handle assembly. Manipulation of the distal portion of the lead or catheter may be accomplished by rotating the handle while advancing or retracting the slide member, thereby releasing or applying traction to the pull wire and straightening or curving the distal portion of the lead or catheter.

Advantageously, as traction is applied continuously the lever provides a mechanical advantage of 2:1 or more between the force needed to pull the wire directly and the force needed to operate the slide member. This reduces the mechanical force to be applied by the fingers and also allows the slide member to be temporarily fixed in one location with the application of an external force. A continuous, dynamic range of curvature from zero to at least two hundred seventy degrees may be induced in the distal portion of the lead or catheter. Thus a very small movement of the slide member in relation to the body of the manipulative handle causes a large change in curvature of the distal portion of the lead or catheter. The 2:1 mechanical advantage of the lever expands this range of control motion of the slide member and allows for increased fineness of control of the stylet curvature.

In addition, through a series of apertures along the stylet body, the stylet may be bent in three dimensions, e.g. as a helix. Lateral displacement of the pull wire outside the lumen of the tubular member is restrained, in one embodiment, within the lumen of the lead, by the lead conductor, or the catheter wall. In a further embodiment lateral displacement of the pull wire outside the lumen of the tubular member is restrained by a retainer. This therefore limits contact and therefore friction between pull wire and the lead conductor or catheter wall which, as discussed above, may lead to pull wire breakage as well as limit lead or catheter rotation about the stylet.

BRIEF DESCRIPTION OF THE DRAWINGS

These and other objects, advantages and features of the invention will become more apparent and the invention will be more fully understood by reference to the drawings of the preferred embodiments thereof, wherein:

FIG. 1 is a perspective view illustrating the steerable stylet and manipulative handle assembly of the present invention.

FIG. 2 is a side elevation view of the manipulative handle assembly portion of the present invention depicting the slide member advanced distally to release traction to the pull wire and thus straightening the distal portion of the steerable stylet.

FIG. 3 is a side elevation view of the manipulative handle assembly portion of the present invention with the slide member retracted proximally to apply traction to the pull wire and impart curvature to the distal portion of the steerable stylet.

FIG. 8 is a top view of the first embodiment of the distal portion of the stylet of the present invention.

FIG. 9 is a cross-sectional view of the elongated tubular member and pull wire along lines A—A of FIG. 8.

FIG. 10 is a cross-sectional view of the elongated tubular member and pull wire taken along lines B—B of FIG. 8.

FIG. 11 is a cross-sectional view of a die and tool for deforming the distal portion of the tubular member shown in FIG. 8.

FIG. 12 is a top view of a distal portion of a further embodiment of the steerable stylet of the present invention.

FIG. 13 is a side view of the embodiment shown in FIG. 12.

FIG. 17 is a top view of the distal section of the embodiment shown in FIG. 15.

FIG. 18 is a cross-sectional view of the embodiment shown in FIG. 17 along the line 18—18.

DESCRIPTION OF THE PREFERRED EMBODIMENTS

Figure 7:
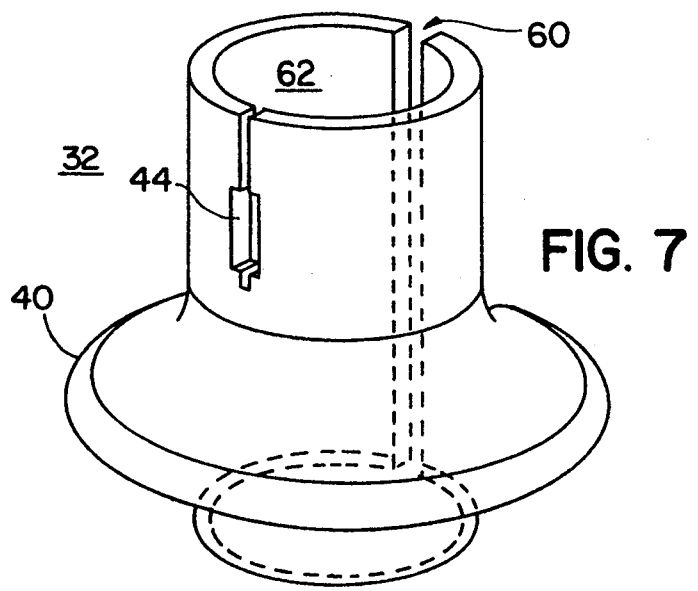
FIG. 7 is a perspective view of the slide member of the manipulative handle assembly portion of the present invention.

As described above, the steerable stylet and manipulative handle assembly of the present invention may be advantageously employed either for introducing an intravascular electrical sensing and/or stimulation lead, such as a transvenous or endocardial pacing or cardioversion lead, or a tubular catheter, such as a drug deliver, sensor-bearing, or lead removal catheter assembly. The specific leads or catheters are not within the scope of the present invention and, to the extent they are discussed, are only described in reference to their cooperation with the stylet and manipulative handle assembly of the present invention.

Turning now to FIG. 1, it illustrates a perspective view of the steerable stylet and manipulative handle assembly 1 of the present invention assembled together and illustrating a certain degree of curvature imparted in the distal end thereof through retraction of pull wire 12 in relation to the elongated tubular member 10. The steerable stylet and manipulative handle assembly 1 comprises elongated tubular member 10 and pull wire 12 having proximal portion or section 14 and distal portion or section 16 with an elongated intermediate section extending therebetween (not specifically illustrated.) Distal section 16 possesses first and second apertures or openings 18, 20 separated apart span 15. As described hereafter, span 15 comprises a predetermined distance preferably in the range of 2.0 to 4.0 inches. This may further include the distal straight section extending between second opening 20 and distal tip or end 22. The radius of curvature to be imparted as pull wire 12 is retracted proximally is preferably between 0.50 and 1.5 inches although other dimensions can also be used.

Pull wire 12 mechanically cooperates with distal tip or end 22 of tubular member 10 and extends within lumen 13 of tubular member 10, out second opening 20 and alongside tubular member 10 at span 15, whereupon it extends through first opening 18 and proximally through lumen 13 of tubular member 10 to proximal section 14. Pull wire 12 is only fixedly attached to tubular member 10 at distal end 22 and, in certain embodiments, it may extend distally from distal end 22 and terminate in an enlarged element having a diameter greater than the inside diameter of lumen 13.

Turning now to the manipulative handle 28, it includes housing 30 (preferably cylindrical), slide member 32, lever 34 and spring wire clip element 36 which are attached to proximal section 14 of the steerable stylet 2. In this regard, tubular member 10 is mechanically attached to opening 33 in neck-down portion 38 of housing 30 and terminates therewithin. Pull wire 12 extends within housing 30 and is mechanically coupled to lever 34 as illustrated more completely in FIGS. 2 and 3. The manipulative handle 28 may be removably attached to steerable stylet 2, including pull wire 12, thereby permitting manipulative handle 28 to be reusable in conjunction with a disposable steerable stylet 2.

In use, tubular member 10 and pull wire 12 are inserted into connector pin opening of a lead (not shown) which is axially arranged with the lumen within the lead body itself (also not shown), in a fashion well-known fashion in the art, or into the lumen of a catheter. A press fit of inside portion of neck-down portion 38 with the outside surface of lead connector pin opening or the catheter lumen opening is relied upon to hold the lead or catheter in fixed relation with housing 30. After this mechanical connection is effected, the lead or catheter may be rotated by rotation of housing 30, and curvature may be imparted by slide member 32 acting on lever 34 and pull wire 12. The overall dimensions of housing 30 and slide member 32 are configured to fit within physician's hand so as to allow thumb engagement with circular ridge 40 to move slide member 32 back and forth on housing 30 to increase or decrease the radius of curvature in distal portion 16 of the stylet assembly. Friction between the outer surface of housing 30 and the inner surface of slide member 32 is relied on to hold lever 34 in a desired position.

Turning now to FIGS. 2 and 3, side elevation, phantom line, views of manipulative handle 28 in the relaxed and fully tractioned positions of slide member 32 and lever 34 in relation to housing 30 and certain internal broken line components thereof are illustrated, respectively. Essentially, lever 34 (shown individually in FIG. 6) is pivoted at its fixed end 35 on clip 36, and its free end 37, captured by slot 44 in the top surface of slide member 32, is pivoted back and forth by movement within an elongated channel 42 in housing 30. Proximal end of pull wire 12 is fitted in an opening 39 along the body of lever 34 so that it is pulled back and forth with movement of slide member 32.

Figure 4:
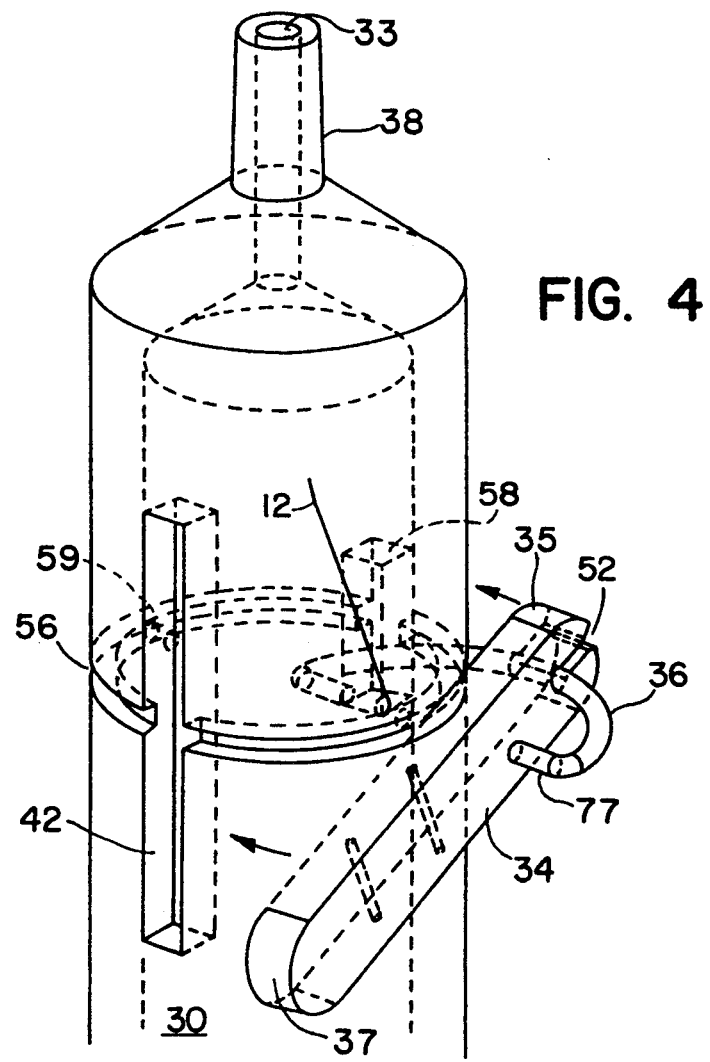
FIG. 4 is a perspective view of the housing of the manipulative handle assembly portion of the present invention showing its internal and external configuration.
Figure 6:
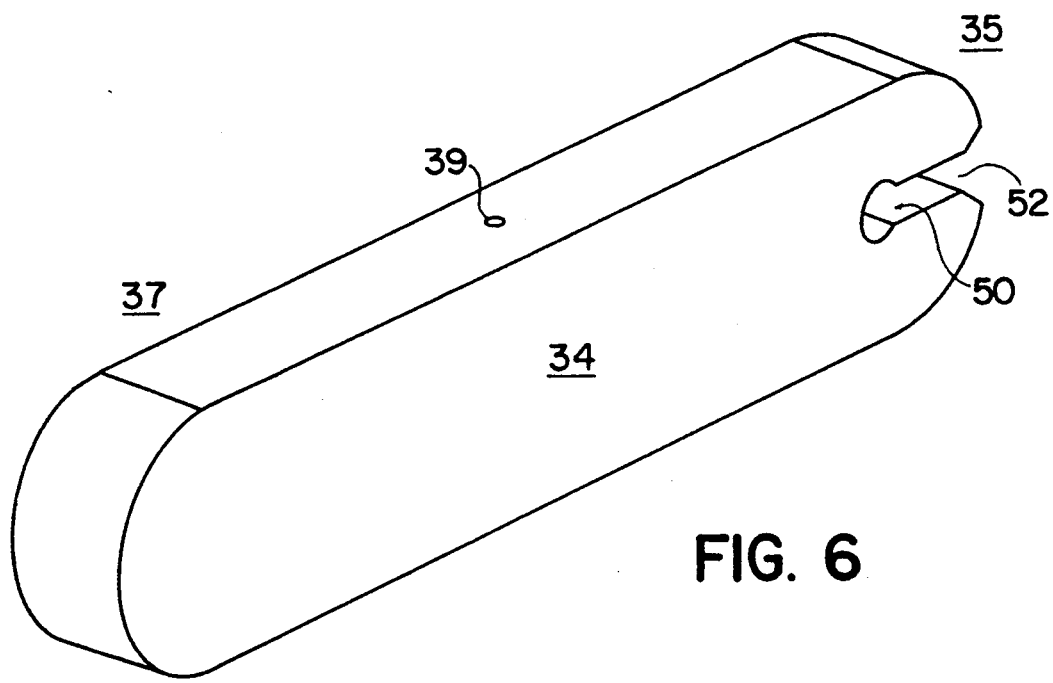
FIG. 6 is a perspective view of the lever used in the housing of the manipulative handle assembly portion of the present invention.

Turning now to FIG. 4, a perspective view of housing 30 illustrates the manner in which lever 34 and clip 36 are interconnected with the proximal end of pull wire 12. Lever 34, shown in FIG. 6, is a flat-sided elongated member having a pair of semicircular shaped ends 35, 37. A clothespin shaped hole 50 and groove 52 in fixed end 35 thereof are adapted to be slipped over clip 36.

Figure 5:
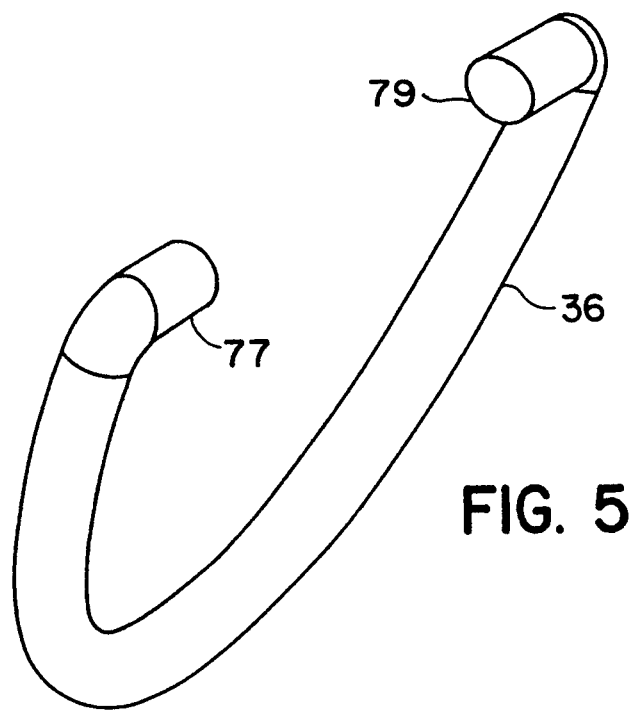
FIG. 5 is a perspective view of a spring clip inserted in a groove in the housing of the manipulative handle assembly portion of the present invention.

Clip 36, shown in FIG. 5, is generally C-shaped and adapted to fit within and wrap about the circumference of groove 56 extending across bottom opening 58 illustrated in FIG. 4. Bottom opening 58 receives the end of lever 34 which snaps onto clip 36 by action of groove 52. The shape and springiness of clip 36 retains it in position once ends 77, 79 of clip 36 are snapped into groove 56 and hole 59 on each side of housing 30. Similarly, lever 34 is snapped into place so that hole 50 fits around the exposed portion of clip 36 traversing bottom opening 58 of housing 30.

Elongated channel 42 in housing 30 extends a distance sufficient to provide the desired degree of movement of lever 34 and pull wire 12 with regard to tubular member 10.

Referring now to FIG. 7, perspective view of slide member 32 illustrates slot 44 for receiving free end 37 of lever 34 and moving it back and forth within channel 42 of housing 30 as well as opening 60 within which the other end of lever 34 is accommodated in assembly shown in FIGS. 2 and 3.

Preferably, inside diameter 62 of slide member 32 is undersized somewhat with respect to the outside diameter of housing 30 so that friction may be relied upon to hold slide member 32 in any position shown in FIGS. 1–3 while lead and stylet assembly are advanced, withdrawn or rotated by the physician in manipulating the position of the distal end of the lead or catheter.

A further embodiment of manipulative handle 28 for use with the steerable stylet described herein may be seen in the application of Fideler entitled "Steerable Stylet Handle" filed Apr. 28, 1993, Ser. No. 08/055,947 and incorporated herein by reference.

Turning now to FIGS. 8–13, first and second preferred embodiments of distal portion 16 of the stylet assembly shown in FIG. 1 are illustrated. In these embodiments, it is anticipated that tubular member 10 is constructed of hypodermic needle tubing, such as 304W stainless steel tubing having an outside diameter in the range of 0.012 to 0.016 inches with about 0.0035 inch wall thicknesses. Pull wire 12 is preferably 0.005–0.007 inch stainless steel wire and has high tensile strength.

The first preferred embodiment of forming first and second openings 18, 20 and the deformation of span 15 of tubular member 10 extending therebetween is illustrated in FIGS. 8–11. In this embodiment, span 15 of tubular member 10 is indented, preferably longitudinally, between openings 18, 20 to provide a weakened section which will bend, generally between openings 18, 20, as pull wire 12 is drawn taut. Deformation by indentation also renders the tubing in this section more resistant to kinking and better able to flex. Of course other deformations in tubular member 10 along span 15 such as a concavity, flattened surface, furrow, or other configurations which permit tubular member 10 to bend along span 15 without readily kinking may also be used and be within the scope of the present invention.

Distal portion 16 illustrated in FIG. 8 includes first and second openings 18, 20, distal tip 22 and pull wire 12 extending from its point of attachment 23, made in distal tip 22, out second opening 20, alongside deformed section 11 of span 15 and back into lumen 13 through first opening 18.

Figure 26:
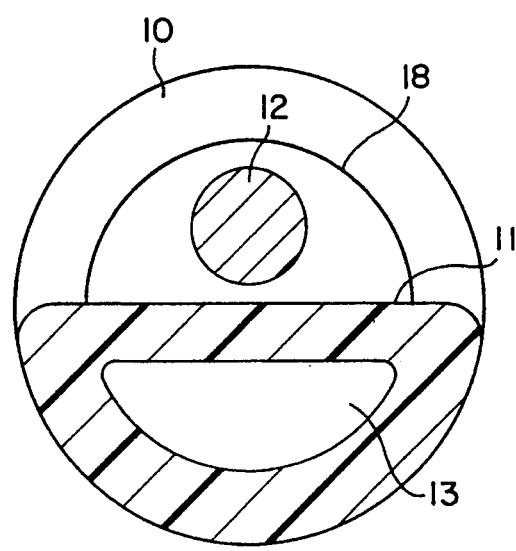
FIG. 26 is a cross-sectional view of an additional embodiment of the present invention showing the elongated tubular member and pull wire in relation to the deformed section.

A further embodiment is depicted in FIG. 26. As seen this embodiment is substantially similar to that shown in FIGS. 10 and 18 with the exception that tubular member 10 is merely flattened on one side and not indented along deformed section 11 of span 15. While this structure allows bending generally between openings 18, 20, it has not been found to perform in a manner as acceptable as that shown in FIGS. 10 or 18, although this embodiment is well within the scope of the present invention.

Turning now to FIGS. 9 and 10, they illustrate cross-sectional views of tubular member 10 and pull wire 12 taken along section lines A—A and B—B, respectively. In FIG. 9, pull wire 12 is shown residing within lumen 13 of tubular member 10. In FIG. 11, wire 12 is shown extending from opening 18 in tubular member 10 and distally along deformed section 11 of span 15 of tubular member 10 at the point where the section B—B was taken in FIG. 8. Lumen 13 in that section is compressed substantially.

Turning now to FIG. 11, it depicts a simple die for deforming, such as flattening or indenting or both, at least section 11 of span 15 of distal portion 16 by placing that portion of tube 10 in a groove 70 in elongated block 72, fitting an elongated hardened, preferably hardened steel, pin 74 on top of tubular member 10 within groove 70 and applying force in the direction of arrow 76 to tubular member. Preferably the width of groove 70 is selected to be slightly larger than the outside diameter of tubular member 10. To form the embodiment depicted in FIG. 26 pin 74, however, is flattened on one side to conform with flat surface along section 11.

FIGS. 12 and 13 depict a further alternative manner in which an elongated opening may be obtained. As seen, distal portion 16 of steerable stylet assembly wherein openings 18, 20 and deformed section 11 are replaced by an elongated cutaway portion 11' of tube 10. The elongated cutaway portion 11' shown in FIGS. 12 and 13 is illustrated in the same fashion as FIGS. 8–11 in that the first and second openings 18, 20 are replaced by first and second cuts 18' and 20' respectively and section 11 is cutaway and designated as section 11'.

There is no fixed attachment of pull wire 12 to distal end 22 of tubular member 10 shown in FIGS. 12 and 13. Instead, pull wire 12 is adapted to terminate in having a diameter greater than the inside diameter of lumen 13. This construction allows the same traction forces to be applied as in the fixed end embodiment illustrated in FIGS. 8–10. It also allows for the advantageous use of a rounded end or ball-tip stylet which may reduce perforations of the lumen of the lead body or the thin wall catheter that may be employed with the steerable stylet and manipulative handle assembly 1. Alternative tip designs may be provided to act as keys to engage with active fixation elements which may be rotated out of or extended from the distal end of an active fixation pacing lead in the manner described in the above-referenced '013 patent, for example.

In constructing prototypes of the steerable stylet of the present invention, it was found that the cutaway tubing embodiment shown in FIGS. 12 and 13 was inferior to the indented embodiment of FIGS. 8–11 in resistance to kinking. It has also been found that the indented embodiment is easier to manufacture than the cutaway embodiment. In the course of experimentation, an attempt was also made to fabricate a steerable stylet merely having the first and second spaced apart openings 18, 20 in tubular lead body 10 without either cutting away a portion of body or deforming that portion between two openings. Experiments conducted with pull wire extending outside tube between first and second openings and fixedly attached at distal end thereof showed an unacceptable tendency of tube to kink at even moderate curvatures. Consequently, there is presently a belief that the embodiment of FIGS. 8–11 with either distal end of pull wire 10 crimped to or engaged with distal end 22 of tubular member 10 is preferred to the embodiment of FIGS. 12 and 13 or the unmodified tubular embodiment.

It has been still further found that an embodiment featuring a retainer 82, as shown in FIGS. 15–18 is preferable to the embodiments of FIGS. 10–13. As seen, the embodiment of FIGS. 15–18 employs retainer 82 along distal section 16 having openings 18, 20.

Although the figures, for clarity, show retainer 82 as presenting a greater diameter to stylet 2, retainer 82 and stylet 2 may be configured, such as with tapers or indentations or a combination thereof, to maintain the same or substantially the same diameter in the region of retainer 82. Further, while retainer 82 is depicted as covering the entire span 15 between openings 18, 20, retainer 82 may be fashioned to cover only a portion of span 15 and not cover the entire span 15 between openings 18, 20.

Figure 16:
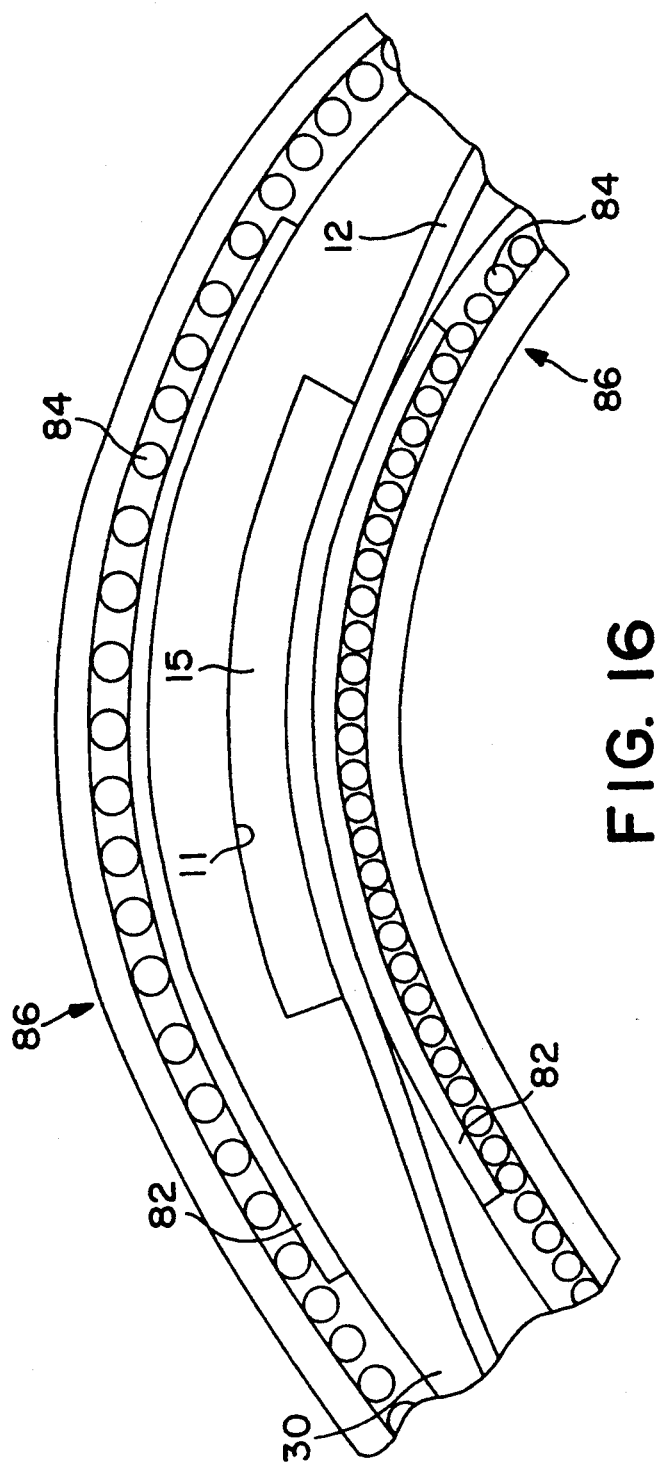
FIG. 16 is a cross-sectional view of a portion of the steerable stylet having an exaggerated bend showing the retainer retaining the pull wire from engaging the lead coils.
Figure 19:
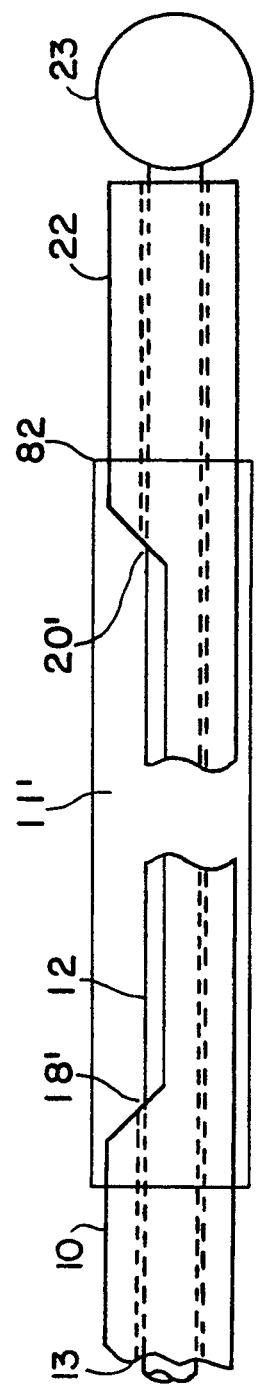
FIG. 19 is a side view of an additional embodiment.
Figure 20:
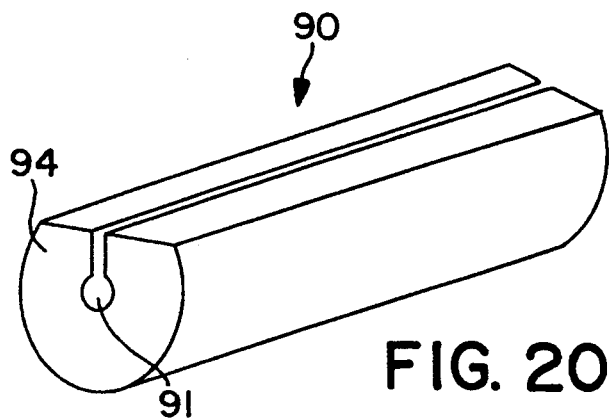
FIG. 20 is a perspective view of the turning knob used to axially rotate a lead with the stylet.
Figure 21:
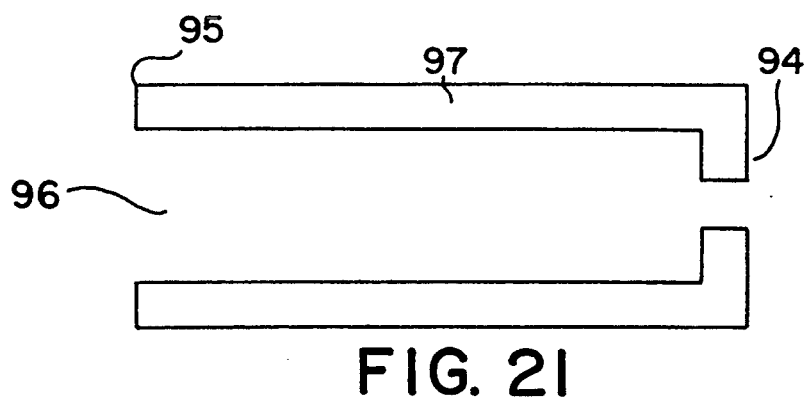
FIG. 21 is a lateral cross-sectional view of the turning knob shown in FIG. 20.
Figure 22:
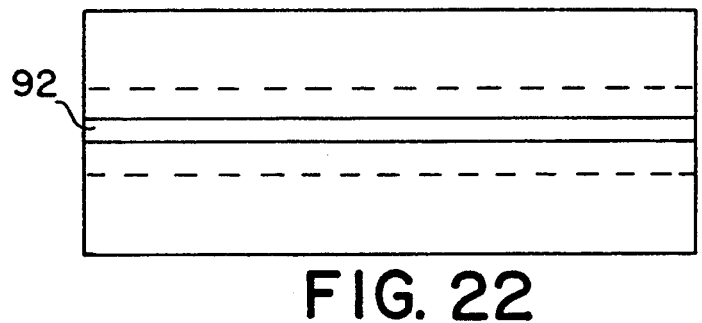
FIG. 22 is a plan view of the top of the turning knob shown in FIG. 20.
Figure 23:
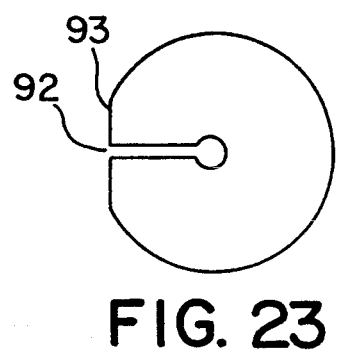
FIG. 23 is a plan end view of the top of the turning knob shown in FIG. 20.
Figure 24:
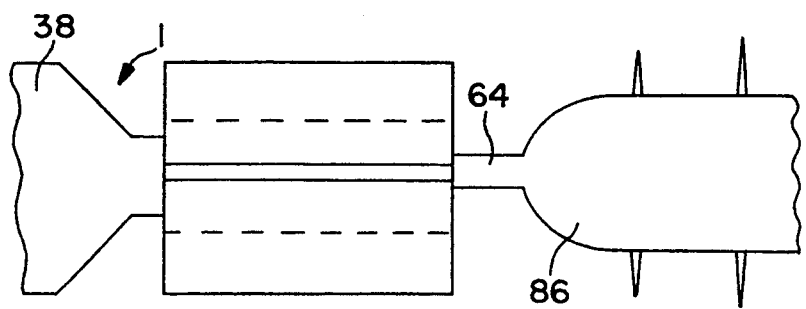
FIG. 24 is a top plan partial sectional view of the turning knob positioned over a steerable stylet of the present invention to rotate a Bisping-type screw-in lead connector.
Figure 25:
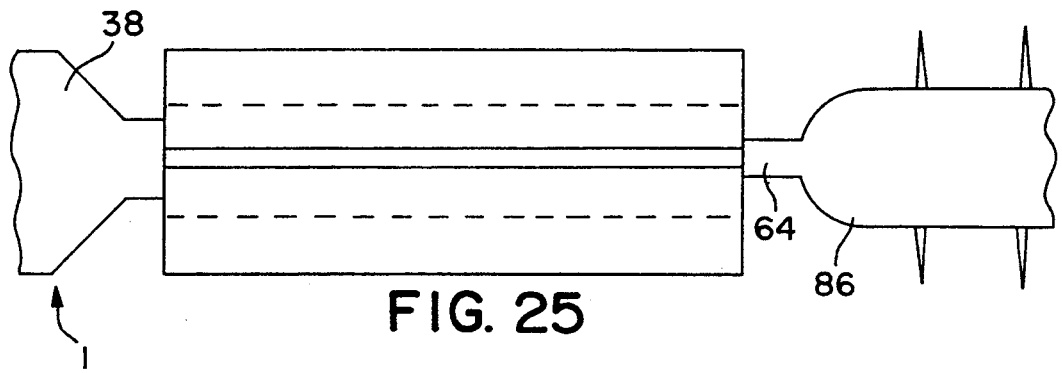
FIG. 25 is a top plan partial sectional view of a second embodiment of a turning knob positioned over a steerable stylet of the present invention to rotate a Bisping-type lead connector.

Retainer 82 functions to retain pull wire 12 and maintain stylet 2 as isodiametric in the region of openings 18, 20 when deflected. Retainer 82 also serves as a lubricous solid layer to facilitate rotation of lead coil 84 around stylet 2 even when deflected, as best seen in FIG. 16. Specifically retainer 82 prevents pull wire 12 from contacting lead coil 84. This is important as it has been found that friction between pull wire 12 and lead coil 84, and plastic deformation of pull wire 12 against lead coil 84, as is permitted by the embodiment depicted in FIG. 10, may lead to premature breakage of pull wire 12, thereby rendering the entire stylet and manipulative handle assembly of the present invention inoperative. A broken pull wire 12, moreover, may jam within the lead coil 84, thereby making the stylet assembly non-removable and the lead unusable. Friction also prevents rotation of the lead coil 84 around the stylet. Such rotation is necessary when placing leads which require rotation around the stylet for fixation. Retainer 82 also facilitates sliding of lead 86 over stylet 2 in a longitudinal direction.

Retainer 82 is preferably constructed from a hard, high elastic modulus, polymeric material, such as polyimide. Retainer 82 may also be constructed from a metal, such as stainless steel or Nitinol. The embodiment of FIG. 18 is manufactured in a similar fashion as the embodiments discussed above, except with the additional step of providing retainer 82 in distal section 16 proximate openings 18, 20.

A further embodiment of the present invention may feature a knob for use with the stylet in positioning screw-in leads. As seen in FIGS. 20–25 knob 90 is adapted to engage and rotate lead pin 64 of a screw-in lead, such as that disclosed in Bisping U.S. Pat. No. 4,106,512 incorporated herein by reference or used in MEDTRONIC Model 4058M bipolar, implantable, screw-in, transvenous lead. Specifically knob 90 has gripping hole 91 which mates with and securely grips lead pin 64 of screw-in lead 86. Slot 92 and central cavity 97 permit knob 90 to be introduced over stylet 2 (not shown) to grip lead pin 64. Opposite distal end 94, proximal end 95 has opening 96. Opening 96 is dimensioned to fit about neck-down portion 38 of stylet handle 28. Knob 90 may be provided in several sizes, preferably so that distal end 94 grips lead pin 64 and proximal end 95 fits about neck-down portion 38 no matter the lead size used. Multiple length knobs thereby permit a single size stylet to be used and still allow a physician to readily rotate lead pin 64 and thereby fix screw-in lead 86 in place, as seen by comparing FIGS. 24 and 25.

As seen turning knob 90 may be rotated by a natural rolling action of the fingers and thumb. Flat surface 93 allows turning knob 90 rotations to be readily indicated and counted without having to look at turning knob 90.

Figure 14:
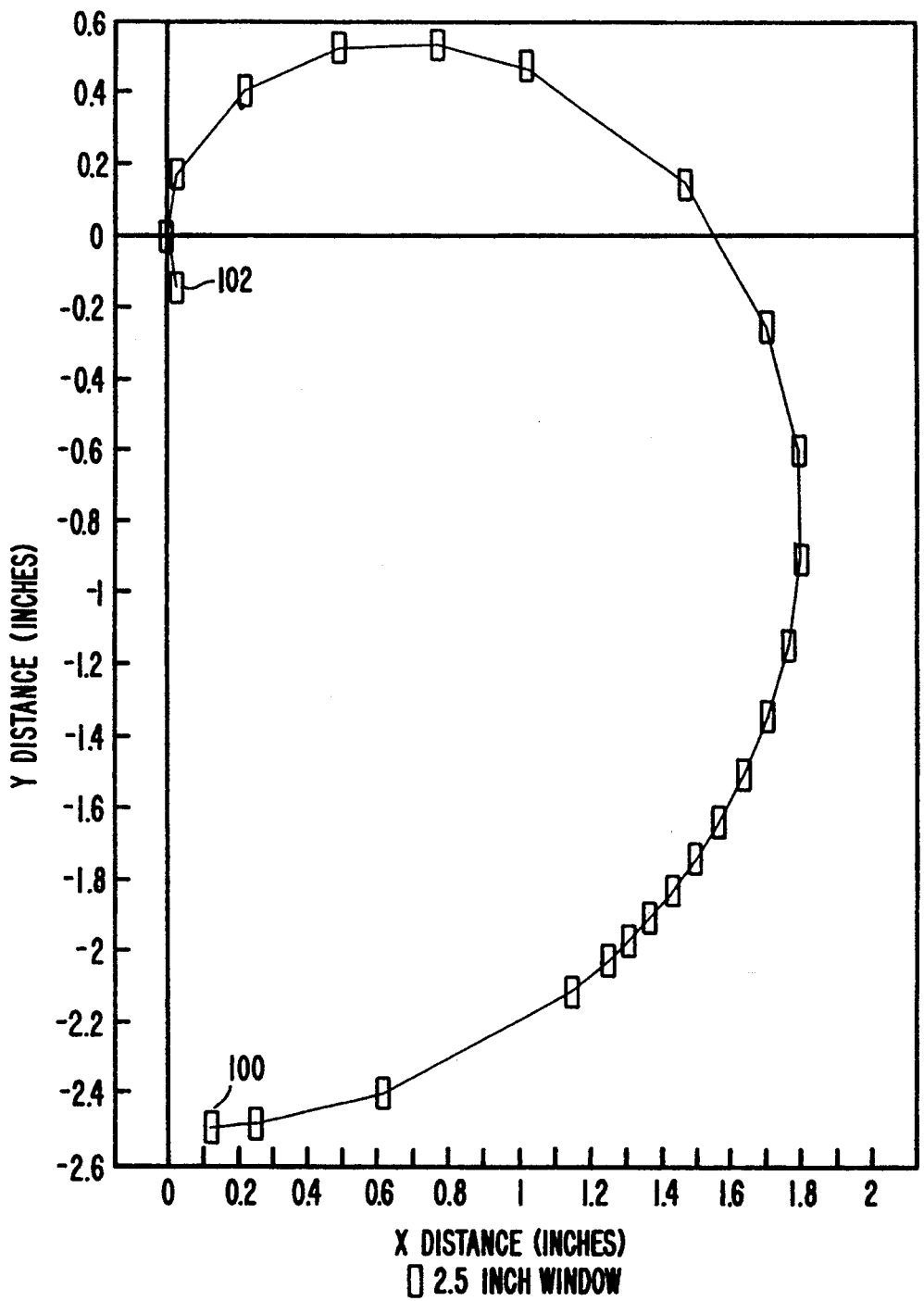
FIG. 14 is an illustration of the dynamic curvature in the X—Y plane imparted by a prototype steerable stylet and manipulative handle assembly in accordance with the teachings of the present invention.
Figure 15:
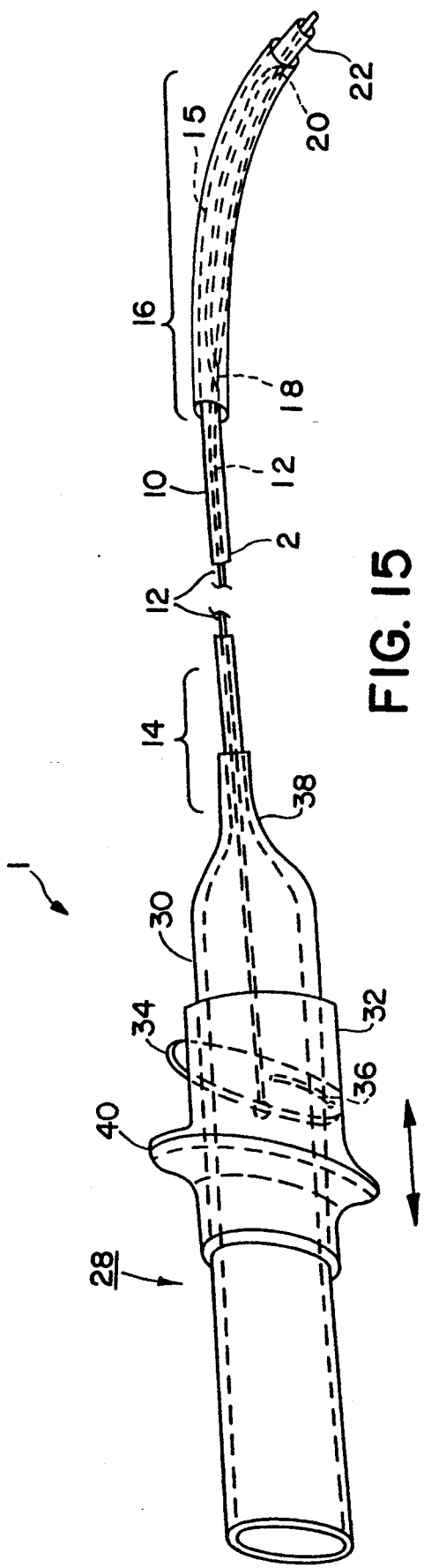
FIG. 15 is a perspective view illustrating a further preferred embodiment of the present invention.

Turning now to FIG. 14, it is an illustration of the dynamic curvature in the X—Y plane imparted by a prototype steerable stylet and manipulative handle assembly 1 in accordance with the teachings of the present invention. In FIG. 14, the origin of coordinates is the beginning of the deflectable part of stylet tubular member 10, and the illustrated points (shown by the rectangles) represent the coordinates of tip 22 at various states of deflection for a stylet with a span having a predetermined distance of 2.5 inches for pull wire 12. The curve represents the locus of all points through which tip 22 will pass as the stylet 1 is dynamically deflected and illustrates that tip 22 may be deflected from straight at point 100 to point 102 where it forms a complete circular loop.

The steerable stylet and manipulative handle assembly 1 described above in conjunction with its preferred embodiments provides the desirable features of stiffness, torque transmission, and dynamic curvature for a range of curvatures desired in use as illustrated (for example) in FIG. 14 with reasonable force and high resistance to kinks. In any given implant procedure, the ability to provide dynamic curvature changes avoids withdrawing the stylet to change its curvature as the lead is passed. The one-handed manipulation of the handle facilitates the achievement of dynamic curvature while advancing and rotating the lead or catheter. In animal tests, it was found that the dynamic curvature facilitated the locating and passage of the distal portion of a pacing lead into the coronary sinus with unaccustomed ease. Further the one-handed operation of a screw-in lead afforded by use of the steerable stylet and manipulative handle assembly 1 and turning knob 90 further facilitates a reliable and ready placement of a lead in a patient.

The embodiments as described include only a single deformed, such as cutaway, flattened or indented, section 11 of span 15 of tubular member 10 and pull wire 12 extending the predetermined distance extra-lumenally thereby. It will be understood that in certain applications, it may be desirable to provide for at least one further span or at least one further aperture thereof along the length of the stylet. In addition at least one further span or aperture may be located along different planes, thereby enabling the stylet to be deflected along different planes, e.g. as a helix.

While the embodiment of the present invention has been described in particular application to leads and catheters, it will be understood the invention may be practiced in other technologies where the aforementioned characteristics are desirable.

The invention has been described in detail with particular reference to the preferred embodiments thereof, but it will be understood variations and modifications can be effected within the scope of the following claims.

What is claimed is:

1. A stylet and manipulative handle assembly controllable to form selected curvatures in a distal portion of a catheter or lead having a lumen extending therethrough, comprising:

an elongated tubular member having proximal and distal portions thereof and having an internal lumen said tubular member having a first side opening between said internal lumen and an external surface of said tubular member, and a second side opening, a span of said tubular member extending between said first side opening and said second side opening, said tubular member being deformed in cross-section along said span;

at least one traction element extending through said internal lumen, said traction element having a distal end and a proximal end, said distal end attached to said distal portion of said tubular member, said proximal end projecting from said proximal portion of said tubular member, said traction element extending through said first side opening and along said external surface of said tubular member; and a manipulative handle attached to said proximal portion of said tubular member and to said proximal end of said traction element for exerting tension on said traction element at said proximal end to form said tubular element to a desired degree of curvature depending upon the amount of tension and whereby said distal portion of said catheter or lead is similarly curved, wherein said manipulative handle comprises:

a longitudinal housing having a distal end thereof attached to said proximal portion of said tubular member and receiving said proximal end of said traction element therewithin;

a lever coupled for pivotal motion and adapted to be disposed transversely at least partially within said housing;

means for attaching said proximal end of said traction element to said lever; and a slide member coupled to said lever and adapted to slide upon said longitudinal housing for advancing and retracting a portion of said lever and thereby releasing and applying traction to said traction element to release or induce curvature in said distal portion of said elongated tubular member.

2. The assembly of claim 1 wherein said span is deformed by at least one longitudinal indentation.

3. The assembly of claim 1 wherein said span is deformed by flattening a portion of said span and whereby a cross-section of said span has a flat first portion and a semi-circular second portion.

4. The assembly of claim 1 wherein said span has a concave depression.

5. The assembly of claim 1 further comprising a retainer proximate said traction element extending along said external surface of said tubular member, said retainer limiting said traction element from contacting said catheter or lead when traction is applied to said traction element.

6. The assembly of claim 1 further comprising a turning knob, said turning knob having a central channel and a gripping portion, said central channel adapted to fit said turning knob about a stylet and a lead connector, said gripping portion adapted to grip a lead connector, said turning knob further having a first surface indicative of a turn position of said turning knob.

7. The assembly of claim 1 wherein said manipulative handle is removably attached to said tubular members.

8. A stylet and manipulative handle assembly for insertion into a lumen of a hollow elongated catheter or lead body for imparting a curvature in a portion thereof, said stylet assembly comprising:
  a two piece stylet adapted to be inserted into said lumen, said stylet comprising;
  a tubular member having proximal and distal ends and proximal and distal portions, said proximal end having a proximal opening, at least one side opening in said distal portion;
  a pull wire extending within said tubular member through said proximal opening therein and through said at least one side opening and extending along a span, said tubular member deformed by at least one longitudinal indentation in at least a portion of said span;
  means for engaging said pull wire with said distal end of said tubular member and to mechanically couple said pull wire and said tubular member together; and
  a manipulative handle coupled to the proximal end of said tubular member and receiving said pull wire, said manipulative handle further comprising means for applying traction to said pull wire in said proximal direction to induce a curvature in said tubular member and in the adjacent elongated catheter or lead body.

9. The assembly of claim 8 wherein means for applying traction to said pull wire in said proximal direction to induce a curvature in said tubular member and in the adjacent elongated catheter or lead body further comprises:
  a longitudinal housing having a distal end thereof attached to said proximal portion of said tubular member and receiving said proximal end of said pull wire therewithin;
  a lever coupled for pivotal motion and adapted to be disposed transversely at least partially within said housing;
  means for attaching said proximal end of said pull wire to said lever; and
  a slide member coupled to said lever and adapted to slide upon said longitudinal housing for advancing and retracting a portion of said lever and thereby releasing and applying traction to said pull wire to release or induce curvature in said distal portion of said tubular member.

10. The assembly of claim 8 wherein said span is deformed by flattening a portion of said span and whereby a cross-section of said span has a flat first portion and a semi-circular second portion.

11. The assembly of claim 8 wherein said span is deformed by removing a portion of said span proximate in a region where said pull wire extends through said at least one side opening and extends along said span.

12. The assembly of claim 8 wherein said span has a concave depression.

13. The assembly of claim 8 further comprising a retainer proximate said pull wire extending along said external surface of said tubular member, said retainer limiting said pull wire from contacting said catheter or lead body when traction is applied to said pull wire.

14. The assembly of claim 8 further comprising a turning knob, said turning knob having a central channel and a gripping portion, said central channel adapted to fit said turning knob about said stylet and a lead connector, said gripping portion adapted to grip a lead connector, said turning knob further having a first surface indicative of a turn position of said turning knob.

15. The assembly of claim 8 wherein said deformation of said span is effected by compressing said tubular member upon itself proximate in a region where said pull wire extends through said at least one side opening and extends along said span.

16. A stylet and manipulative handle assembly for insertion into a lumen of a hollow catheter or lead body for imparting a curvature in a portion thereof, said stylet assembly comprising:
  a stylet adapted to be inserted into said lumen, said stylet comprising;
  a tubular member having proximal and distal ends and proximal and distal portions, said proximal end having a proximal opening, said tubular member having a first side opening and a second side opening;
  a pull wire extending within said tubular member, said pull wire extending through said first opening along an exterior span of said tubular member and through said second side opening;
  a retainer retaining said pull wire along said span so said pull wire will not contact said catheter or lead body;
  means for engaging said pull wire with said distal end of said tubular member and to mechanically couple said pull wire and said tubular member together; and
  a manipulative handle coupled to the proximal end of said tubular member and receiving said pull wire, said manipulative handle further comprising means for applying traction to said pull wire in said proximal direction to induce a curvature in said tubular member and in the adjacent elongated catheter or lead body.

17. The assembly of claim 16 wherein means for applying traction to said pull wire in said proximal direction to induce a curvature in said tubular member and in the adjacent elongated catheter or lead body further comprises:
- a longitudinal housing having a distal end thereof attached to said proximal portion of said tubular member and receiving said proximal end of said pull wire therewithin;
- a lever coupled for pivotal motion and adapted to be disposed transversely at least partially within said housing;
- means for attaching said proximal end of said pull wire to said lever; and
- a slide member coupled to said lever and adapted to slide upon said longitudinal housing for advancing and retracting a portion of said lever and thereby releasing and applying traction to said pull wire to release or induce curvature in said distal portion of said tubular member.

18. The assembly of claim 16 wherein said tubular member is deformed in at least a portion of said span.

19. The assembly of claim 18 wherein said deformation of said span is effected by compressing said tubular member upon itself proximate in a region where said pull wire extends through said at least one side opening and extends along said span.

20. The assembly of claim 18 wherein said span is deformed by flattening a portion of said span and whereby a cross-section of said span has a flat first portion and a semi-circular second portion.

21. The assembly of claim 18 wherein said span has at least one longitudinal indentation.

22. The assembly of claim 16 wherein said span has a concave depression.

* * * * *